United States Patent [19]
Long et al.

[11] Patent Number: 5,808,028
[45] Date of Patent: Sep. 15, 1998

[54] MOLECULAR CLONE OF A P58 RECEPTOR PROTEIN AND USES THEREOF

[75] Inventors: Eric O. Long, Rockville, Md.; Nicolai Wagtmann, Washington, D.C.

[73] Assignee: The United States of America as represented by the Department of Health and Human Services, Washington, D.C.

[21] Appl. No.: 248,628

[22] Filed: May 24, 1994

[51] Int. Cl.⁶ .......................... C12N 15/12; C07K 14/705
[52] U.S. Cl. .................... 536/23.5; 435/69.1; 435/252.3; 435/254.11; 435/325; 435/320.1
[58] Field of Search ................................ 435/69.1, 240.1, 435/252.3, 254.11, 320.1, 325; 536/23.1, 23.5

[56] References Cited

PUBLICATIONS

Lewin, Science, vol. 237, 1570, Sep. 25, 1987.
Reeck, Cell, vol. 50, 667, 1987.
Moretta, A. et al. "A Novel Surface Antigen Expressed By a Subset of Human CD3⁻ CD16⁺ Natural Killer Cells" *J. Exp. Med.*, 171:695–714 (1990).
Moretta, L. et al. "Human Natural Killer Cells; Origin, Clonality, Specificity, and Receptors" *Advances in Immunology*, 55:341–380 (1994).

*Primary Examiner*—Sally P. Teng
*Attorney, Agent, or Firm*—Morgan & Finnegan, L.L.P.

[57] ABSTRACT

The present invention provides a purified and isolated nucleic acid molecule encoding the p58 receptor protein. The present invention also provides vectors encoding this nucleic acid molecule, a host cell stably transformed or transfected with the vector, as well as the p58 receptor protein produced by this host cell. The present invention further provides methods for detecting nucleic acid encoding the p58 receptor as well as the p58 receptor protein in biological samples, methods for identifying a ligand capable of binding to the p58 receptor protein, and methods for screening for drugs capable of acting as agonists or antagonists to the p58 receptor protein. The present invention also provides the agonists and antagonists identified by the screening methods, as well as their use. Lastly, the present invention provides chimeric protein comprising the cytoplasmic region of a p58 receptor protein.

9 Claims, 1 Drawing Sheet

MOLECULAR CLONE OF A P58 RECEPTOR PROTEIN AND USES THEREOF

Natural killer (NK) cells are important in the immune defense against tumors, viruses and intracellular parasites. NK cells also may be involved in the rejection of bone marrow transplants, and other transplants. The ability to intervene with the immune function of the NK cells, by either boosting NK cell responses to pathogens, or by lowering or stopping unwanted NK cell responses, is a long recognized need.

The p58 receptor of NK cells is a family of cell surface molecules with a molecular mass of about 58,000 which is involved in the recognition of target cells by NK cells. The p58 receptor contributes to the specificity of NK cells in their recognition of major histocompatibility complex (MHC) class I molecules on target cells. The specific recognition of MHC molecules mediated by the p58 receptor protects the target cell from lysis by the NK cell. Conversely, absence of the appropriate MHC class I molecule on target cells leads to NK-mediated lysis.

Prior to the present invention, however, no members of the p58 family have been purified sufficiently to permit their isolation and characterization. This is because it is impossible to grow large enough populations of the NK cells to permit isolation of sufficient amounts of p58 receptor protein for sequencing. Furthermore, the known NK cell lines express high levels of Fc receptor which could interfere with immunoaffinity purifications utilizing monoclonal antibodies directed to the p58 receptor protein, since these antibodies also bind to the Fc receptor.

In particular, Moretta, et al. (1990) described the use of a monoclonal antibody designated GL183 to immunoprecipitate either a 58 Kd band or a broad 55–58 Kd band from NK clones which had been labeled with $^{125}$I (Moretta, et al. *J. Exp. Med.* 171: 695–714 (1990); Moretta, et al. *Advances in Immunology* 55: 341–380 (1994)). However, Moretta, et al. did not sufficiently purify the alleged p58 receptor protein to permit its isolation and characterization, and could not have done so utilizing the particular NK cells described therein, or known NK cells.

This is because NK cells described in Moretta, et al., as most NK cells, cannot be grown to large enough populations to permit isolation of sufficient amounts of p58 receptor protein for sequencing. Specifically, about $1 \times 10^{10}$ NK cells would have to be obtained in order to purify an amount of pure p58 protein sufficient for sequencing. However, NK cells cannot be expanded much beyond $1 \times 10^7$ cells since they do not grow well in culture.

Moreover, the NK cell lines described in Moretta, et al. express high levels of Fc receptor which could interfere with immunoaffinity purifications utilizing the GL183 monoclonal antibody, since this antibody also binds to the Fc receptor. Furthermore, the inventors of the present invention found that the p58 and Fc receptors (CD16) have very similar isoelectric points and relative masses, which could make their separation difficult.

The inventors of the present invention overcame the potential problems in the art by employing a long term NK cell line designated NK 3.3 which, unlike previously identified NK clones, grows well under long-term culture conditions, can be readily expanded to sufficient numbers, and expresses very low levels of the Fc receptor. Accordingly, the inventors of the present invention were the first to purify a member of the p58 receptor family, characterize it, and subsequently clone its DNA.

SUMMARY OF THE INVENTION

The present invention provides a purified and isolated nucleic acid molecule encoding the p58 receptor protein.

The present invention also provides vectors encoding this nucleic acid molecule, a host cell stably transformed or transfected with the vector, as well as the p58 receptor protein produced by this host cell.

The present invention also provides a method for detecting nucleic acid encoding the p58 receptor in a biological sample which comprises the steps of: (a) contacting nucleic acid from the biological sample with the probe made from nucleic acid encoding the p58 receptor protein under conditions permitting a complex to be formed between the probe and nucleic acid presence in the sample; and (b) detecting the formation of the complex.

The present invention further provides a method for detecting nucleic acid encoding the p58 receptor in a biological sample which comprises the steps of: (a) contacting nucleic acid from the biological sample with a sense and an antisense primer prepared from nucleic acid encoding the p58 receptor protein under conditions permitting PCR amplification to occur; and (b) detecting amplification of the nucleic acid from the biological sample.

Moreover, the present invention provides a method for detecting a p58 receptor protein in a biological sample which comprises the steps of: (a) contacting the biological sample with a reagent which specifically reacts with a p58 receptor protein; and (b) detecting the formation of a complex between the protein and the reagent.

The present invention also provides a method for identifying a ligand capable of binding to the p58 receptor protein which comprises the steps of: (a) contacting a p58 receptor protein or cells which express the p58 receptor protein with a candidate ligand; and (b) detecting the formation of a complex between the p58 receptor protein and the ligand.

In addition, the present invention provides a method for identifying a ligand capable of binding to the p58 receptor protein which comprises the steps of: (a) contacting a p58 receptor protein with cells transfected with cDNA encoding a candidate ligand; and (b) detecting the formation of a complex between the p58 receptor protein and the ligand expressed by the cells.

Also provided by the present invention is a method for screening for drugs capable of acting as agonists or antagonists to the p58 receptor protein which comprises the steps of: (a) contacting cells which express the p58 receptor protein with candidate drugs; and (b) evaluating the biological activity mediated by said contact.

The present invention also provides the agonists and antagonists identified by the method above as well as uses of these agonists and antagonists.

In particular, the present invention provides a method for preventing immunosuppressive rejection of a transplant in a subject receiving the transplant which comprises administering to the subject an amount of an agonist to a p58 receptor protein effective to prevent immunosuppressive rejection of the transplant.

The present invention also provides a method for treating a neoplastic cell growth in a subject in need of such treatment which comprises administering an amount of an antagonist to a p58 receptor protein effective to treat the neoplastic cell growth.

Lastly, the present invention provides a chimeric protein comprising (a) the cytoplasmic region of a p58 receptor protein which transmits a dominant negative signal to a cell expressing the p58 receptor protein; and (b) a transmembrane domain and an extracellular domain of a known receptor.

BRIEF DESCRIPTION OF THE FIGURES

FIGS. 1A–1C. Transfection of the 183c16 cDNA leads to cell surface expression of the monoclonal antibody GL183. 183 refers to the molecule recognized by the GL183 mab. FACS analysis of 183 expression at the surface with the 183 cDNA is shown.

DETAILED DESCRIPTION OF THE INVENTION

The present invention provides a purified and isolated nucleic acid molecule encoding the p58 receptor protein. The nucleic acid molecule includes all nucleic acid sequences which encode for the p58 receptor including all degenerate forms. The term "nucleic acid" includes but is not limited to DNA, RNA or cDNA.

In the preferred embodiment, the p58 receptor protein has the nucleotide sequence contained in SEQ ID NO:1, or a sequence which is substantially homologous thereto. "Substantially homologous" as used herein refers to substantial correspondence between the nucleic acid sequences of various members of the p58 receptor protein family. "Substantially homologous" means at least 50% identical, preferably about 65% identical, and most preferably, about 70–90% identical. The nucleic acid is mammalian, and is preferably human or murine.

The nucleic acid sequences for the additional members of the p58 receptor protein family may be isolated by screening libraries of cDNA clones derived from NK cell RNA with a probe corresponding to the sequence contained in SEQ ID NO:2 using standard DNA hybridization techniques. It is expected that the DNA sequences encoding the different members of the p58 receptor protein family will exhibit a level of similarity that clearly exceeds the 55% identity required for cross-hybridization. This is because analogous families of related genes encoding other receptors usually display similarities with about 70 to 90% identity among different members (e.g. HLA class I genes, HLA class II genes, genes encoding different T cell receptors, genes encoding different immunoglobulin molecules).

Furthermore, genomic clones encoding the p58 receptor family also may be isolated by screening human genomic libraries with a probe corresponding to the sequence contained in SEQ ID NO:2 using standard DNA hybridization techniques.

In addition, the corresponding gene in mice may be isolated by cross-hybridization techniques as long as some portion of the probe above has at least 55% nucleotide sequence identity with the mouse genes. If cross-hybridization is not successful, oligonucleotide primers based on the same sequence may be used to isolate the mouse genes using PCR. The mouse genes may be used to generate "knock-out" mice with a defect in one or several of the genes encoding the mouse counterpart of the human p58 receptor protein. Such knock-out mice would be extremely valuable tools to study the role of p58 receptors in immune responses.

The present invention also provides a vector comprising the nucleic acid molecule encoding the p58 receptor protein, as described above. In the preferred embodiment, the vector is an expression vector which comprises at least one expression control element operationally linked to the nucleic acid sequence encoding the p58 receptor. The expression control elements are inserted in the vector to control and regulate the expression of the nucleic acid sequence, and are known in the art. The vectors of the present invention may be constructed by known techniques (see U.S. Pat. Nos. 4,704,362, 4,366,246, 4,425,437, 4,356,270, and 4,571,421), using commercially available plasmids.

The present invention also provides a host cell stably transformed or transfected with the vector above. The host cells may be prokaryotic such as E. coli, or eukaryotic such as animal, plant, insect and yeast cells. The host cells are stably transformed or transfected by known procedures (see U.S. Pat. Nos. 4,704,362, 4,366,246, 4,425,437, 4,356,270, and 4,571,421). In the particularly preferred embodiment, amplification protocols (e.g. methotrexate selection with dhfr vectors) may be used to obtain cells that produce high levels of recombinant proteins. Other expression systems based on virus vectors may be used for extremely high level expression, but only transiently (e.g. baculovirus, Sindbis virus). The host cells may be screened for clones which produce the recombinant p58 receptor protein by known procedures such as Coomassie blue staining and Western blotting.

It is also within the confines of the present invention that modified forms of the p58 receptor protein may be engineered and produced. Truncated or mutated forms can be produced to define functional domains of the p58 receptor protein. Secreted forms can be engineered for the production of soluble receptors.

The present invention also provides the p58 receptor protein produced by the host cell above. The recombinant protein expressed by the host cells may be obtained as a crude lysate or can be purified by standard protein purification procedures known in the art such as differential precipitation, molecular sieve chromatography, ion-exchange chromatography, isoelectric focusing, gel electrophoresis, affinity chromatography, immunoaffinity chromatography, and the like.

Preferably, the p58 receptor protein has the amino acid sequence contained in SEQ ID NO:2, or is a biologically active analogue thereof. The phrase "biologically active analogue thereof" refers to proteins having substantially homologous sequences to the sequence contained in SEQ ID NO:2, and possess similar activity as that protein. The isolated and purified p58 receptor protein of the present invention includes all members of the p58 receptor protein family.

The present invention also provides a method for detecting nucleic acid encoding the p58 receptor protein in a biological sample utilizing as probes the nucleic acid above, or portions thereof, labeled with detectable markers. In particular, the method comprises the steps of: (a) contacting the probe with a biological sample under conditions permitting a complex to be formed between the probe and nucleic acid present in the sample; and (b) detecting the formation of the complex.

The biological samples include mammalian tissue or cell samples. The nucleic acid may be extracted from the biological samples by known procedures. Specifically, the cells may be lysed using an enzyme such as proteinase K, in the presence of detergents such as sodium dodecyl sulfate (SDS), NP40, or Tween 20. If the nucleic acid is genomic DNA, it may be extracted using known techniques such as phenol/chloroform extraction, or other procedures (see U.S. Pat. Nos. 4,900,677 and 5,047,345). Alternatively, the DNA may be isolated using one of the commercially available kits such as the Oncor Genomic DNA isolation kit. RNA may be extracted using various known procedures such as guanidinium thiocyanate followed by centrifugation in cesium chloride (Sambrook, J., Fritsch, E. F., and Maniatis, T. "Molecular Cloning, A Laboratory Manual," second edition, Cold Spring Harbor Laboratory Press, pp. 7.0–7.25 (1989)).

The formation of the complex may be detected using various conventional techniques known in the art including but not limited to Northern blotting, Southern blotting, dot and slot hybridization, S1 nuclease assay, ribonuclease protection assay, and filter hybridization (Southern, E. M. *J. Mol. Biol.* 98:503 (1975); Chirgwin, J. M., et al. *Biochemistry* 18: 5294–5299 (1979); Kafatos, et al. *Nuc. Acids. Res.* 7: 1541 (1979); Thomas, P. S. *Proc. Natl. Acad. Sci.* 77: 5201 (1980); White, B. A. and F. C. Bancroft *J. Bio. Chem.* 257: 8569 (1982); Berk, A. J. and P. A. Sharp *Cell* 12: 721 (1977); Casey, J. and N. Davidson *Nuc. Acids Res.* 4:1539 (1977); Sambrook, J., Fritsch, E. F., and Maniatis, T. "Molecular Cloning, A Laboratory Manual," second edition, Cold Spring Harbor Laboratory Press, pp. 7.30–7.87 and 9.31–9.62 (1989)).

In the method above, the probe is labeled with a detectable marker which includes but is not limited to fluorescence, enzyme or radiolabeled markers such as $^{32}$P and biotin. In the preferred embodiment, the marker is $^{32}$P. The probe is labeled by known procedures such as phosphorylation with bacteriophage T4 polynucleotide kinase (Sambrook, J., Fritsch, E. F., and Maniatis, T. "Molecular Cloning, A Laboratory Manual," second edition, Cold Spring Harbor Laboratory Press, pp. 11.31–11.32 (1989)).

It is within the confines of the present invention that probes may be designed to detect all members of the p58 family, or may be unique in detecting only one or more specific members of the p58 family.

The present invention also provides a method for detecting nucleic acid encoding the p58 receptor in a biological sample using standard PCR procedures. In this regard, the method comprises the steps of: (a) contacting nucleic acid from the biological sample with a sense and an antisense primer prepared from the sequence of the present invention under conditions permitting PCR amplification to occur; and (b) detecting amplification of the nucleic acid from the biological sample.

Polymerase chain reaction is performed by methods and conditions disclosed in U.S. Pat. Nos. 4,683,202 and 4,683,195 and in Perkin Elmer Cetus PCR kit protocols. The DNA polymerase, deoxyribonucleotide triphosphates (dNTPS) (e.g. dATP, dCTP, dTTP, and dGTP), and amplification buffer (e.g. glycerol, tris-hydrochloric acid, potassium chloride, Tween 20, and magnesium chloride) are readily commercially available (Perkin Elmer Cetus). The polymerase chain reaction may be performed as many cycles as desired. Reverse transcription (RT) of mRNA and RT-PCR are performed by methods described in commercially available kits such as the RT and RT-PCR kits (Perkin Elmer Cetus).

The sense and antisense primers for use in PCR and RT-PCR may be prepared from the nucleic acid sequence above using automated instruments sold by a variety of manufacturers or may be commercially synthesized.

It is within the confines of the present invention that primers may be designed to detect all members of the p58 family, or may be unique in detecting only one or more specific members of the p58 family.

The present invention also provides a method for detecting a p58 receptor protein in a biological sample using particular reagents which specifically react with the p58 receptor protein.

The term "reagent" includes monoclonal or polyclonal antibodies. Exemplary antibody molecules for use in the detection methods of the present invention are intact immunoglobulin molecules, substantially intact immunoglobulin molecules, or those portions of an immunoglobulin molecule that contain the antigen binding site, including those portions known in the art as F(ab), F(ab'), F(ab')$_2$, and F(v). In the preferred embodiment, antibodies specific to each different member of the p58 receptor protein family, or portions thereof, may be used to detect expression of their corresponding p58 receptor protein family member. The complete protein or unique portions thereof of the particular members of the p58 family may be utilized as an immunogen, with or without a carrier molecule, to produce these antibodies. Examples of carrier molecules includes human albumin, bovine albumin, keyhole limpet hemocyanin, and the like.

Polyclonal and monoclonal antibodies, or their fragments, may be produced by methods known in the art, or by genetic engineering (Kohler and Milstein (1975) *Nature* 256: 495–497; Campbell "Monoclonal Antibody Technology," the "Production and Characterization of Rodent and Human Hybridomas" in Burdon, et al. (eds.) (1985) "Laboratory Techniques in Biochemistry and Molecular Biology," Volume 13, Elsevier Science Publishers, Amsterdam).

The antibodies are used in immunoassays to detect the p58 receptor protein in biological samples. In particular, the method comprises the steps of: (a) contacting the biological sample with an antibody; and (b) detecting the formation of a complex between the protein and the antibody. In the particularly preferred embodiment, the immunoassays are used to detect different members of the p58 receptor protein family in the biological sample using their respective antibodies.

Suitable immunoassays include but are not limited to radioimmunoassay, Western blot assay, immunofluorescent assay, enzyme immunoassay, chemiluminescent assay, and immunohistochemical assay. These assays may be performed using procedures well known in the art. (In "Principles and Practice of Immunoassay" (1991) Christopher P. Price and David J. Neoman (eds), Stockton Press, New York, N.Y.; Ausubel, et al. (eds) (1991) in "Current Protocols in Molecular Biology" John Wiley and Sons, New York, N.Y.).

Target cells that do not express a cell surface ligand able to interact with the p58 receptor expressed by a particular NK cell are likely to be lysed by that NK cell. This deadly fate results from the fact that the p58 receptor on NK cells serves to provide a negative signal to the NK cell and thus stop the lytic machinery of the NK cell. Rejection of bone marrow transplants, and possibly autoimmune reactions, are mediated by NK cells when the negative signal fails to be delivered to the NK cells. It is therefore very important, and potentially very useful clinically, to determine exactly which molecules on target cells serve as ligands for the p58 receptor proteins and as protective elements on target cells that would otherwise be killed.

Therefore, the present invention also provides a method for identifying a ligand capable of binding to the p58 receptor protein. In one embodiment, the method comprises the steps of: (a) contacting a p58 receptor protein or cells which express the p58 receptor protein with a candidate ligand; and (b) detecting the formation of a complex between the p58 receptor protein and the ligand. In another embodiment, the method comprises the steps of: (a) contacting a p58 receptor protein with cells transfected with cDNA encoding a candidate ligand; and (b) detecting the formation of a complex between the p58 receptor protein and the ligand expressed by the cells.

The term "ligand" refers to any protein or proteins that may interact with the p58 receptor protein. Said ligand may be soluble or membrane bound. The ligand may be a naturally occurring protein, or synthetically or recombinantly produced. The ligand may also be a nonprotein molecule that acts as a ligand when it interacts with the p58 receptor. In the preferred embodiment, the ligands are HLA class I molecules and their isotypes. Interactions between the ligand and receptor include but are not limited to covalent or non-covalent interactions. The receptor binding domain is any region of the receptor that interacts directly or indirectly with the ligand.

The p58 receptor protein is preferably recombinant p58 receptor protein, and most preferably is soluble. It is within the confines of the present invention that the soluble recombinant molecules may be produced as fusion proteins with a secreted form of immunoglobulin. This leads to efficient expression of a secreted soluble form and also to detection using well-established antibodies specific for the immunoglobulin molecules. The soluble p58-immunoglobulin fusion proteins may be used as reagents for analysis by flow cytometry to test for the presence of ligands on different cells.

Cells stably transfected with a complete cDNA encoding a p58 receptor protein may be used to test binding of soluble ligands or binding of immobilized ligands. To increase valency, ligands may be attached to a support such as a latex bead. These assays are known in the art as rosette formation assays.

The present invention also provides a method for screening for drugs capable of acting as agonists or antagonists to the p58 receptor protein which comprises the steps of: (a) contacting cells which express the p58 receptor protein with candidate drugs; and (b) evaluating the biological activity mediated by said contact.

The term "drugs" includes but is not limited to proteins, peptides, agents purified from conditioned cell medium, organic molecules, inorganic molecules, antibodies oligonucleotides, or analogs of the ligand described above. The drug may be naturally occurring or synthetically or recombinantly produced. Specific agonists of the p58 receptor protein would be extremely useful in preventing unwanted NK-mediated lysis of target cells (e.g. in bone marrow transplantation). Specific antagonists would be useful for boosting NK cell responses to unwanted pathogens such as cancer cells.

The term "biological activity" as used herein means the triggering of the p58 receptor protein to transmit a negative signal to the cell which expresses it. This is evaluated by tranfecting the cDNA encoding the p58 receptor protein with known reporter gene constructs, and measuring the triggering effect of specific drugs on the p58 receptor protein using known calorimetric assays (e.g. beta-galactosidase) or luminometry (e.g. luciferase).

The present invention also provides an agonist or antagonist to a p58 receptor protein identified using the methods above, as well as uses thereof.

In particular, the present invention provides a method for preventing immunosuppressive rejection of a transplant in a subject receiving the transplant which comprises administering to the subject an amount of an agonist to a p58 receptor protein effective to prevent immunosuppressive rejection of the transplant.

As used herein, the term "transplant" refers to any cell, tissue or organ which may be suspectable to immunosuppressive rejection when transplanted into a patient. In the preferred embodiment, the transplant is bone marrow.

The present invention also provides a method for treating a neoplastic cell growth in a subject in need of such treatment which comprises administering an amount of an antagonist to a p58 receptor protein effective to treat the neoplastic cell growth.

The term "neoplastic cell growth" includes any of the known cancers such as cancers of the breast, lung, brain, groin, and the like. The term "treatment" includes the partial or total inhibition of neoplastic cell growth, as well as the partial or total destruction of the neoplastic cells. The term "subject" includes a human or animal subject diagnosed as having cancer. It is within the confines of the present invention that the antagonist may be administered in conjunction with an antibody which specifically recognizes the tumor.

The administration for both methods above may be affected by means known to those skilled in the art such as oral, rectal, topical intravenous, subcutaneous, intramuscular, or intraperitoneal routes of administration.

The dosage form and amount for each method can be readily established by reference to known immunosupressive treatments and antineoplastic treatments, respectively. The actual dose will depend upon the route of administration, the pharmacokinetic properties of the individual treated, as well as the results desired.

Studies of chimeric receptor proteins consisting of extracellular domain of one receptor and the intracellular domain of a different receptor indicate that a common mechanism of signal transduction through the cell membrane is shared by different growth factor receptors (Riedel, et al. *Nature* 324: 68–70 (1986); Riedel, et al. *EMBO J.* 8: 2943–2954 (1989)). The specificity of the signal transmitted by the receptors resides in the intracellular domain. Chimeras between the extracellular domain of a known ligand and intracellular domain of an orphan receptor can be activated by the known ligand, yet the biological function elicited is similar to the receptor with the intracellular domain. Numerous chimeric receptors including insulin receptor (IR)/epidermal growth factor receptor (EGFR) (Riedel, et al. *Nature* 324: 68–70 (1986), EGFR/IR (Riedel, et al. *EMBO J.* 8: 2943–2954 (1989)), platelet-derived growth factor receptor beta (PDGFR-beta)/fibroblast growth factor receptor-1 (FGFR-1) (Mares, et al. *Growth Factors* 6:93–101 (1992)) have been constructed and elicited proper responses.

Accordingly, the present invention also provides a chimeric protein comprising (a) the cytoplasmic region of a p58 receptor protein which transmits a dominant negative signal to a cell expressing the p58 receptor protein; and (b) a transmembrane domain and an extracellular domain of a known receptor. This chimeric protein may be constructed as described in the publications above. The chimeric protein is useful for studying the recognition of target molecules mediated by the p58 receptor protein family.

The present invention is described in the following Experimental Details section, which sets forth specific examples to aid in an understanding of the invention, and should not be construed to limit in any way the invention as defined in the claims which follow thereafter.

EXPERIMENTAL DETAILS SECTION

A. Purification of p58 Receptor Protein

1. NK3.3 Cells Express 183 Ag

The mAb GL183 recognizes a surface antigen (183 antigen, 183 Ag) expressed on a subset of freshly isolated human NK cells and on some NK clones (Moretta, et al. *J. Exp. Med.* 171: 695–714 (1990); Moretta, et al. *Advances in Immunology* 55: 341–380 (1994)). The difficulty of generating and growing human NK clones has precluded the isolation of large amounts of 183 antigen from these cells necessary for sequencing the 183 antigen. Purification also has been hindered because most known NK cells express the Fc receptor (CD16), which also has a similar isoelectric point and molecular mass as the 183 antigen.

The inventors of the present invention have found by FACS analysis using GL183 that a human NK cell line NK3.3 obtained from Jackie Kornbluth (Kornbluth, J., et al. *J. Immunol.* 129:2831 (1982)) expresses the 183 antigen at the cell surface, and also express low levels of the Fc receptor (CD16). Unlike previously identified clones, the NK3.3 cell line also grows well under long term conditions, and can be readily expanded.

Analytical experiments were performed to biochemically characterize the 183 Ag expressed on NK3.3, in order to compare it to the Ag expressed on NK clones. NK3.3 and NK clones were surface iodinated and lysed in lysis buffer containing Triton and protease inhibitors. Immunoprecipitation using GL183 and control antibodies, and analysis of the precipitates on SDS-PAGE indicated that the 183 Ag derived from the two sources were very similar.

2. Immunoprecipitation

GL183 was purified from ascites and coupled to Sepharose CL-2B. These GL183-Sepharose beads were used to immunoprecipitate 183 Ag from detergent lysates of surface iodinated NK3.3. The immuno-precipitates were then incubated in an elution buffer at pH 11.2 to test whether the 183 Ag could be eluted from the beads under those conditions. The eluted material was analyzed on SDS gels followed by autoradiography.

It was found that incubation at pH 11.2 released a I-125 labelled protein of the expected size (MW). However, these experiments also showed that control beads, either unconjugated or conjugated to control Abs, immunoprecipitated large amounts of I-125 labelled proteins, which were also eluted from the beads under these conditions, indicating that extensive preclearing of the detergent lysates would be necessary.

The lysate was therefore passed over four sequential columns containing the following beads: Unconjugated Sepharose CL-2B, Mouse IgG-agarose, L243-Sepharose-CL-2B and finally GL183-Sepharose-CL-2B. The first two columns were strictly preclearing columns. The third, containing beads conjugated to L243, a mAb specific for HLA-DR, served as both a preclearing column and a positive control, since the NK3.3 cells also express HLA-DR. To monitor the purification, small amounts of radio-iodinated NK3.3 was used as a tracer.

A lysate prepared from $2 \times 10^9$ NK3.3 cells and spiked with a second lysate prepared from $6 \times 10^7$ surface-iodinated NK3.3 was passed over the 4 columns described above connected to each other in series. The columns were disconnected and the L243 and the GL183 columns were washed with wash buffer in parallel. The bound proteins were eluted with the elution buffer at pH 11.2 and 50 drops/fraction (about 500 µl/fraction) were collected. Each fraction was immediately neutralized by addition of dilute acetic acid. 2 µl of each fraction was counted in a gamma counter to identify fractions containing peak radioactivity. The material in those fractions containing the most radioactivity was further analyzed.

3. SDS-PAGE and Other Purification

60 µl of each fraction was run in a SDS-PAGE gel which was stained with Coomassie Blue to visualize total protein and then exposed to autoradiography film to detect radiolabeled proteins. A single radiolabeled protein migrating at 58 kD was eluted from the GL183 column and not from the L243 column. Although the autoradiography indicated that the GL183 had been purified to apparent homogeneity, Coomassie-staining revealed the presence of several additional non-radioactive proteins, mostly of lower molecular weight. These non-radioactive contaminants made it necessary to further purify the 183 Ag before subjecting it to sequencing.

Several fractions of affinity-column eluate were pooled, EtOH-precipitated and resuspended in sample buffer. The material was run in a preparative SDS-PAGE gel. The proteins were electrophoretically transferred to a ProBlot PVDF membrane which was stained with Coomassie blue. The band at about 58 kD was cut out and subjected to automated Edman degradation. This yielded an N-terminal sequence of 19 amino acids.

Computer searches of the translated Genbank and Swissprot databases showed that the sequence was unique. However, there was no evidence that the sequence was derived from the 183 Ag, rather than from a contaminant protein with the same electrophoretic mobility.

Other methods were evaluated for further purification. Reverse-phase HPLC was found to resolve the 183 Ag too well, in that it separated the material into several fractions. This fractionation procedure revealed that a contaminant with the same electrophoretic mobility was present in the immunoaffinity-purified 183 Ag. This molecule was not detected in the cell surface-iodinated sample and probably represents an intracellular protein.

Anion-exchange HPLC was also attempted but did not separate the 183 Ag from the contaminants. The 183 Ag also became refractive to N-terminal amino acid sequencing during these procedures.

Accordingly, different wash buffers were evaluated during the affinity-purification step to see if conditions could be found where these contaminants would be removed during the column washes without removing the 183 Ag. The following wash procedure was adopted: After washing overnight with 0,1% Triton X-100, 10 mM Tris-HCL, pH 7.5, 150 mM NaCl, 0,02% NaN$_3$ the columns were washed with 0.1% C12E9, 10 mM Tris-HCL pH 9.0, 500 mM NaCl followed by a final wash with 0.1% $C_{12}E_9$, 10 mM Tris-HCL, pH 7.5, 150 mM NaCl. The wash at pH 9.0 was found to remove significant amounts of contaminants with only small decreases in yield of 183 Ag.

Affinity-purified material from about $4 \times 10^9$ cells was subjected to SDS-gel separation and transfer to Problot as described above. After cutting out the region of the membrane containing 183 Ag, it was subjected to digestion with trypsin. The digest was separated by reverse-phase HPLC using a vydac C-18 column. Aliquots of material from the prominent peaks were analyzed by Matrix-Assisted Laser Desorption Mass Spectrometry and fractions containing one main peak were subjected to Edman degradation. The amino acid sequences of eight tryptic peptides were obtained. Computer searches revealed that these sequences were previously unknown.

B. Cloning cDNA of the p58 Receptor Protein

1. PCR Amplification

Based on the amino acid sequences of the N-terminus and internal tryptic peptides of 183, various oligonucleotide primers for PCR amplification were designed. The use of degenerate primers produced too much non-specific amplifications to be practical. Primers were therefore made with inosine substitutions at positions of maximum degeneracy (183N-FOR32; 183P20-BACK32). However, these inosine-containing products could not be cloned into bacterial plasmids for further analysis. Primers without inosines were therefore used in the re-amplification of the initial PCR product (183P20-BACK32B; 183N-FOR32-B). The best primers used are as follows:

- 183N-FOR32: 5' GGI CCI (C/T)TI GTN AA(A/G) TCN GAA GAG AC 3' (SEQ ID NO:3)
- 183P20-BACK32: 5' IC(G/T) (A/G)CT IA(A/G) (A/G)TG (A/G)TA CAT (A/G)TC ATA 3' (SEQ ID NO:4)
- 183P20-BACK32B: 5' NC(G/T) (A/G)CT NA(A/G) (A/G)TG (A/G)TA CAT (A/G)TC ATA 3' (SEQ ID NO:5)
- 183N-FOR32-B: 5' GGN CCN (C/T)TN GTN AA(A/G) TCN GAA GAG AC 3' (SEQ ID NO:6)

2. Construction and Screening of NK3.3 cDNA Library

Total RNA was isolated from NK3.3 by a scaled-up version of the method of Chomczynksi and Sacchi (*Analytical Biochemistry* 162:156–159 (1987)). Poly(A)+ selection was carried out by two passages of the total RNA over an Oligo(dT) column.

The cDNA library was constructed using a kit from Gibco BRL and was size selected as follows. The cDNA library was amplified, and purified double-stranded plasmid was linearized by digestion with NotI and separated by agarose gel electrophoresis. The gel was cut in 21 sections, each containing DNA of a different size, i.e. with inserts of different length. The DNA was purified from the agarose and an aliquot of each fraction was run on an agarose gel. It was transferred to Genescreen, and hybridization was done using the $^{32}$P-labelled 183 PCR amplification product as probe. This identified the fraction containing inserts corresponding to the PCR amplification product.

This fraction was re-circularized with DNA ligase and transformed into *E. coli*. The bacteria were plated on LB plates and after lifting onto Genescreen discs they were screened with the probed described above. Several positive clones were isolated, and 6 were further characterized by sequencing. The 6 clones turned out to be identical in their sequence.

C. Expression of cDNA

Figure 1A:
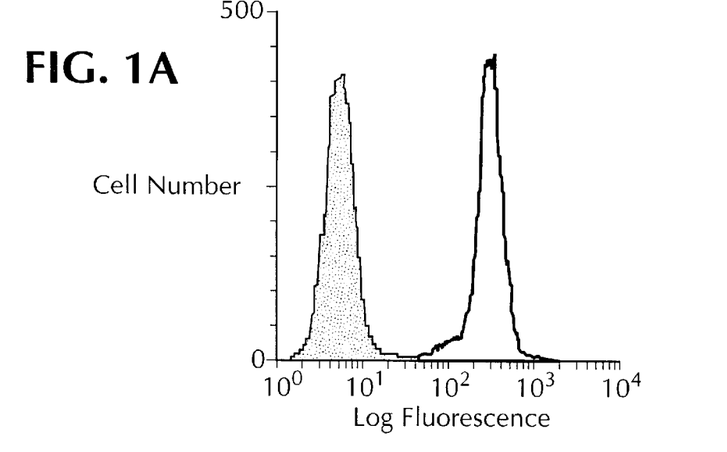
FIG. 1A shows the cell surface expression of 183 (open area) on NK3.3 relative to control staining without primary Ab (Antibody) (filled area). The human T cell line Jurkat does not express 183 (FIG. 1B, filled area), nor does a human B-LCL (FIG. 1 C, filled are). Stable transfection of these two cell lines with the 183c16 cDNA in the eukaryotic expression vector RSV.5(gpt) results in surface expression of 183 (FIGS. 1B and 1C, open areas).
Figure 1B:
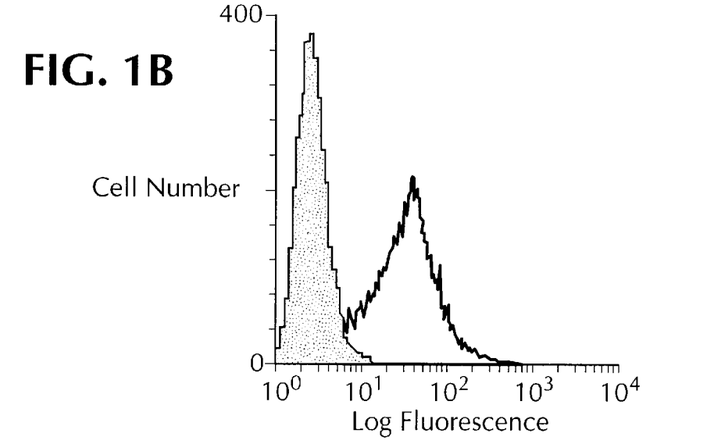
Figure 1C:
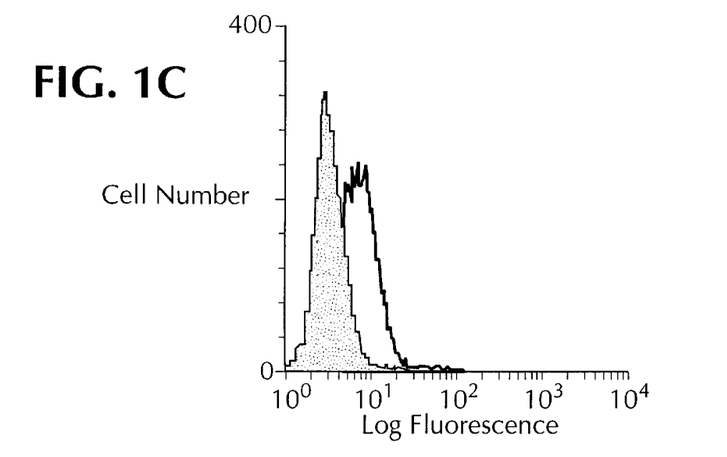

The insert from one of the clones was subcloned into the eukaryotic expression vector RSV.5(gpt). This construct was transfected into the human T cell line Jurkat and into a human B-LCL by electroporation. Stable transfectants were selected by culture in medium containing Mycophenolic acid and Xanthine and were screened for surface expression of 183 Ag by FACS analysis using the GL183 as primary antibody followed by FITC-conjugated rabbit anti-mouse IgG (see FIGS. 1B–1C). The results show that the p58 cDNA directs the surface expression of the 183 Ag in transfected cells.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

---

What is claimed is:

1. A purified and isolated nucleic acid molecule encoding a human p58 receptor protein.

2. The nucleic acid molecule of claim 1, said molecule encoding a p58 receptor protein having an amino acid sequence shown in SEQ ID NO:2.

3. The nucleic acid molecule of claim 2, said molecule having a nucleic acid sequence shown in SEQ ID NO:1.

4. A vector comprising a nucleic acid molecule encoding a human p58 receptor protein.

5. The vector of claim 4, wherein the nucleic acid molecule encodes a p58 receptor protein having an amino acid sequence shown in SEQ ID NO:2.

6. The vector of claim 5, wherein the nucleic acid molecule has a nucleic acid sequence shown in SEQ ID NO:1.

7. A host cell stably transformed or transfected with the vector of claim 5.

8. A host cell stably transformed or transfected with the vector of claim 6.

9. A host cell stably transformed or transfected with the vector of claim 4.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1594 BASE PAIRS
        ( B ) TYPE: NUCLEIC ACID
        ( C ) STRANDEDNESS: SINGLE
        ( D ) TOPOLOGY: UNKNOWN     ( i i ) MOLECULE TYPE:
        ( A ) DESCRIPTION: cDNA to mRNA     ( i i i ) HYPOTHETICAL: NO     ( i v ) ANTI-SENSE: NO     ( v i ) ORIGINAL SOURCE:
        ( A ) ORGANISM: HUMAN
        ( C ) INDIVIDUAL ISOLATE: NK 3.3 CELL     ( x i ) SEQUENCE DESCRIPTION:SEQ ID NO:1:

```
CCTGTCTGCA  CAGACAGCAC  C  ATG  TCG  CTC  ATG  GTC  GTC  AGC  ATG            45
                           Met  Ser  Leu  Met  Val  Val  Ser  Met
                            1                    5

GTG  TGT  GTT  GGG  TTC  TTC  TTG  CTG  CAG  GGG  GCC  TGG  CCA  CAT          87
Val  Cys  Val  Gly  Phe  Phe  Leu  Leu  Gln  Gly  Ala  Trp  Pro  His
 10                        15                        20
```

| | | | | | | | | | | | | | |
|---|---|---|---|---|---|---|---|---|---|---|---|---|---|
| GAG | GGA | GTC | CAC | AGA | AAA | CCT | TCC | CTC | CTG | GCC | CAC | CCA | GGT | 129
| Glu | Gly | Val | His | Arg | Lys | Pro | Ser | Leu | Leu | Ala | His | Pro | Gly |
| | | 25 | | | | 30 | | | | | 35 | | |

| CCC | CTG | GTG | AAA | TCA | GAA | GAG | ACA | GTC | ATC | CTG | CAA | TGT | TGG | 171
| Pro | Leu | Val | Lys | Ser | Glu | Glu | Thr | Val | Ile | Leu | Gln | Cys | Trp |
| | | | 40 | | | | 45 | | | | | | 50 |

| TCA | GAT | GTC | AGG | TTT | CAG | CAC | TTC | CTT | CTG | CAC | AGA | GAA | GGG | 213
| Ser | Asp | Val | Arg | Phe | Gln | His | Phe | Leu | Leu | His | Arg | Glu | Gly |
| | | | | 55 | | | | | | 60 | | | |

| AAG | TTT | AAG | GAC | ACT | TTG | CAC | CTC | ATT | GGA | GAG | CAC | CAT | GAT | 255
| Lys | Phe | Lys | Asp | Thr | Leu | His | Leu | Ile | Gly | Glu | His | His | Asp |
| 65 | | | | | 70 | | | | | 75 | | | |

| GGG | GTC | TCC | AAG | GCC | AAC | TTC | TCC | ATC | GGT | CCC | ATG | ATG | CAA | 297
| Gly | Val | Ser | Lys | Ala | Asn | Phe | Ser | Ile | Gly | Pro | Met | Met | Gln |
| | 80 | | | | | 85 | | | | | 90 | | |

| GAC | CTT | GCA | GGG | ACC | TAC | AGA | TGC | TAC | GGT | TCT | GTT | ACT | CAC | 339
| Asp | Leu | Ala | Gly | Thr | Tyr | Arg | Cys | Tyr | Gly | Ser | Val | Thr | His |
| | | 95 | | | | | 100 | | | | | 105 | |

| TCC | CCC | TAT | CAG | TTG | TCA | GCT | CCC | AGT | GAC | CCT | CTG | GAC | ATC | 381
| Ser | Pro | Tyr | Gln | Leu | Ser | Ala | Pro | Ser | Asp | Pro | Leu | Asp | Ile |
| | | | 110 | | | | | 115 | | | | | 120 |

| GTC | ATC | ACA | GGT | CTA | TAT | GAG | AAA | CCT | TCT | CTC | TCA | CGC | CAG | 423
| Val | Ile | Thr | Gly | Leu | Tyr | Glu | Lys | Pro | Ser | Leu | Ser | Arg | Gln |
| | | | | 125 | | | | | 130 | | | | |

| CCG | GGC | CCC | ACG | GTT | CTG | GCA | GGA | GAG | AGC | GTG | ACC | TTG | TCC | 465
| Pro | Gly | Pro | Thr | Val | Leu | Ala | Gly | Glu | Ser | Val | Thr | Leu | Ser |
| 135 | | | | | 140 | | | | | 145 | | | |

| TGC | AGC | TCC | CGG | AGC | TCC | TAT | GAC | ATG | TAC | CAT | CTA | TCC | AGG | 507
| Cys | Ser | Ser | Arg | Ser | Ser | Tyr | Asp | Met | Tyr | His | Leu | Ser | Arg |
| | | 150 | | | | | 155 | | | | | 160 | |

| GAG | GGG | GAG | GCC | CAT | GAA | CGT | AGG | TTC | TCT | GCA | GGG | CCC | AAG | 549
| Glu | Gly | Glu | Ala | His | Glu | Arg | Arg | Phe | Ser | Ala | Gly | Pro | Lys |
| | | 165 | | | | | 170 | | | | | 175 | |

| GTC | AAC | GGA | ACA | TTC | CAG | GCC | GAC | TTT | CCT | CTG | GGC | CCT | GCC | 591
| Val | Asn | Gly | Thr | Phe | Gln | Ala | Asp | Phe | Pro | Leu | Gly | Pro | Ala |
| | | | 180 | | | | | 185 | | | | | 190 |

| ACC | CAC | GGA | GGA | ACC | TAC | AGA | TGC | TTC | GGC | TCT | TTC | CGT | GAC | 633
| Thr | His | Gly | Gly | Thr | Tyr | Arg | Cys | Phe | Gly | Ser | Phe | Arg | Asp |
| | | | | 195 | | | | | 200 | | | | |

| TCT | CCA | TAC | GAG | TGG | TCA | AAC | TCG | AGT | GAC | CCA | CTG | CTT | GTT | 675
| Ser | Pro | Tyr | Glu | Trp | Ser | Asn | Ser | Ser | Asp | Pro | Leu | Leu | Val |
| 205 | | | | | 210 | | | | | 215 | | | |

| TCT | GTC | ACA | GGA | AAC | CCT | TCA | AAT | AGT | TGG | CCT | TCA | CCC | ACT | 717
| Ser | Val | Thr | Gly | Asn | Pro | Ser | Asn | Ser | Trp | Pro | Ser | Pro | Thr |
| | | 220 | | | | | 225 | | | | | 230 | |

| GAA | CCA | AGC | TCC | GAA | ACC | GGT | AAC | CCC | AGA | CAC | CTG | CAT | GTT | 759
| Glu | Pro | Ser | Ser | Glu | Thr | Gly | Asn | Pro | Arg | His | Leu | His | Val |
| | | 235 | | | | | 240 | | | | | 245 | |

| CTG | ATT | GGG | ACC | TCA | GTG | GTC | ATC | ATC | CTC | TTC | ATC | CTC | CTC | 801
| Leu | Ile | Gly | Thr | Ser | Val | Val | Ile | Ile | Leu | Phe | Ile | Leu | Leu |
| | | | 250 | | | | | 255 | | | | | 260 |

| CTC | TTC | TTT | CTC | CTT | CAT | CGC | TGG | TGC | TGC | AAC | AAA | AAA | AAT | 843
| Leu | Phe | Phe | Leu | Leu | His | Arg | Trp | Cys | Cys | Asn | Lys | Lys | Asn |
| | | | | 265 | | | | | 270 | | | | |

| GCT | GTT | GTA | ATG | GAC | CAA | GAG | CCT | GCA | GGG | AAC | AGA | ACA | GTG | 885
| Ala | Val | Val | Met | Asp | Gln | Glu | Pro | Ala | Gly | Asn | Arg | Thr | Val |
| 275 | | | | | 280 | | | | | 285 | | | |

| AAC | AGG | GAG | GAC | TCT | GAT | GAA | CAA | GAC | CCT | CAG | GAG | GTG | ACA | 927
| Asn | Arg | Glu | Asp | Ser | Asp | Glu | Gln | Asp | Pro | Gln | Glu | Val | Thr |
| | | 290 | | | | | 295 | | | | | 300 | |

| | | | | | | | | | | | | | |
|---|---|---|---|---|---|---|---|---|---|---|---|---|---|
| TAT | GCA | CAG | TTG | AAT | CAC | TGC | GTT | TTC | ACA | CAG | AGA | AAA | ATC | 969 |
| Tyr | Ala | Gln | Leu | Asn | His | Cys | Val | Phe | Thr | Gln | Arg | Lys | Ile | |
| | | 305 | | | | 310 | | | | | | 315 | | |
| ACT | CGC | CCT | TCT | CAG | AGG | CCC | AAG | ACA | CCC | CCA | ACA | GAT | ATC | 1011 |
| Thr | Arg | Pro | Ser | Gln | Arg | Pro | Lys | Thr | Pro | Pro | Thr | Asp | Ile | |
| | | | 320 | | | | | 325 | | | | | 330 | |
| ATC | GTG | TAC | ACG | GAA | CTT | CCA | AAT | GCT | GAG | CCC | TGATCC | | | 1050 |
| Ile | Val | Tyr | Thr | Glu | Leu | Pro | Asn | Ala | Glu | Pro | | | | |
| | | | | 335 | | | | | 340 | | | | | |

```
AAAGTTGTCT  CCTGCCCATG  AGCACCACAG  TCAGGCCTTG  AGGGGATCTT          1100
CTAGGGAGAC  AACAGCCCTG  TCTCAAAACT  GGGTTGCCAG  CTCCAATGTA          1150
CCAGCAGCTG  GAATCTGAAG  GCGTGAGTCT  GCATCTTAGG  GCATCGCTCT          1200
TCCTCACACC  ACAAATCTGA  ACGTGCCTCT  CCCTTGCTTA  CAAATGTCTA          1250
AGGTCCCCAC  TGCCTGCTGG  AGAGAAAACA  CACTCCTTTG  CTTAGCCCAC          1300
AATTCTCCAT  TTCACTTGAC  CCCTGCCCAC  CTCTCCAACC  TAACTGGCTT          1350
ACTTCCTAGT  CTACTTGAGG  CTGCAATCAC  ACTGAGGAAC  TCACAATTCC          1400
AAACATACAA  GAGGCTCCCT  CTTAACACGG  CACTTAGACA  CGTGCTGTTC          1450
CACCTTCCCT  CATGCTGTTC  CACCTCCCCT  CAGACTAGCT  TTCAGCCTTC          1500
TGTCAGCAGT  AAAACTTATA  TATTTTTAA   AATAATTTCA  ATGTAGTTTT          1550
CCCTCCTTCA  AATAAACATG  TCTGCCCTCA  AAAAAAAAAA  AAAA                1594
```

( 2 ) INFORMATION FOR SEQ ID NO:2:

( i ) SEQUENCE CHARACTERISTICS:
            ( A ) LENGTH: 341 AMINO ACIDS
            ( B ) TYPE: AMINO ACID
            ( C ) STRANDEDNESS: UNKNOWN
            ( D ) TOPOLOGY: UNKNOWN        ( i i ) MOLECULE TYPE:
            ( A ) DESCRIPTION: PROTEIN        ( i i i ) HYPOTHETICAL: NO        ( v i ) ORIGINAL SOURCE:
            ( A ) ORGANISM: HUMAN
            ( C ) INDIVIDUAL ISOLATE: NK 3.3 CELL        ( x i ) SEQUENCE DESCRIPTION:SEQ ID NO:2:

```
Met  Ser  Leu  Met  Val  Val  Ser  Met  Val  Cys  Val  Gly  Phe  Phe
 1              5                         10

Leu  Leu  Gln  Gly  Ala  Trp  Pro  His  Glu  Gly  Val  His  Arg  Lys
15                       20                        25

Pro  Ser  Leu  Leu  Ala  His  Pro  Gly  Pro  Leu  Val  Lys  Ser  Glu
         30                       35                       40

Glu  Thr  Val  Ile  Leu  Gln  Cys  Trp  Ser  Asp  Val  Arg  Phe  Gln
              45                       50                       55

His  Phe  Leu  Leu  His  Arg  Glu  Gly  Lys  Phe  Lys  Asp  Thr  Leu
                   60                       65                       70

His  Leu  Ile  Gly  Glu  His  His  Asp  Gly  Val  Ser  Lys  Ala  Asn
                        75                       80

Phe  Ser  Ile  Gly  Pro  Met  Met  Gln  Asp  Leu  Ala  Gly  Thr  Tyr
85                       90                        95

Arg  Cys  Tyr  Gly  Ser  Val  Thr  His  Ser  Pro  Tyr  Gln  Leu  Ser
         100                      105                      110

Ala  Pro  Ser  Asp  Pro  Leu  Asp  Ile  Val  Ile  Thr  Gly  Leu  Tyr
              115                      120                      125
```

Glu Lys Pro Ser Leu Ser Arg Gln Pro Gly Pro Thr Val Leu
            130                     135                 140

Ala Gly Glu Ser Val Thr Leu Ser Cys Ser Ser Arg Ser Ser
            145                     150

Tyr Asp Met Tyr His Leu Ser Arg Glu Gly Glu Ala His Glu
155                 160                     165

Arg Arg Phe Ser Ala Gly Pro Lys Val Asn Gly Thr Phe Gln
    170                 175                     180

Ala Asp Phe Pro Leu Gly Pro Ala Thr His Gly Gly Thr Tyr
        185                 190                     195

Arg Cys Phe Gly Ser Phe Arg Asp Ser Pro Tyr Glu Trp Ser
            200                     205                 210

Asn Ser Ser Asp Pro Leu Leu Val Ser Val Thr Gly Asn Pro
            215                     220

Ser Asn Ser Trp Pro Ser Pro Thr Glu Pro Ser Ser Glu Thr
225                     230                 235

Gly Asn Pro Arg His Leu His Val Leu Ile Gly Thr Ser Val
    240                     245                 250

Val Ile Ile Leu Phe Ile Leu Leu Leu Phe Phe Leu Leu His
        255                 260                     265

Arg Trp Cys Cys Asn Lys Lys Asn Ala Val Val Met Asp Gln
            270                     275                 280

Glu Pro Ala Gly Asn Arg Thr Val Asn Arg Glu Asp Ser Asp
                285                     290

Glu Gln Asp Pro Gln Glu Val Thr Tyr Ala Gln Leu Asn His
295                     300                 305

Cys Val Phe Thr Gln Arg Lys Ile Thr Arg Pro Ser Gln Arg
    310                     315                     320

Pro Lys Thr Pro Pro Thr Asp Ile Ile Val Tyr Thr Glu Leu
        325                     330                 335

Pro Asn Ala Glu Pro
            340

( 2 ) INFORMATION FOR SEQ ID NO:3:

( i ) SEQUENCE CHARACTERISTICS:
        ( A ) LENGTH: 26 BASE PAIRS
        ( B ) TYPE: NUCLEIC ACID
        ( C ) STRANDEDNESS: SINGLE
        ( D ) TOPOLOGY: UNKNOWN     ( i i ) MOLECULE TYPE:
        ( A ) DESCRIPTION: OLIGONUCLEOTIDE     ( i i i ) HYPOTHETICAL: NO     ( i v ) ANTI-SENSE: NO     ( v i ) ORIGINAL SOURCE:
        ( A ) ORGANISM: HUMAN
        ( C ) INDIVIDUAL ISOLATE: NK 3.3 CELL     ( i x ) FEATURE:
        ( A ) NAME/KEY:
        ( B ) LOCATION:
        ( C ) IDENTIFICATION METHOD:
        ( D ) OTHER INFORMATION: The N at nucleotides 3,
            6, and 9 is inosine (I); the N at nucleotide
            7 is C or T; the N at nucleotides 12 and 18
            is C, T, A or G; and the N at nucleotide 15
            is A or G.

( x i ) SEQUENCE DESCRIPTION:SEQ ID NO:3:

GGN CCN NTN GTN AAN TCN GAA GAG AC                                    26

( 2 ) INFORMATION FOR SEQ ID NO:4:

( i ) SEQUENCE CHARACTERISTICS:
        ( A ) LENGTH: 24 BASE PAIRS
        ( B ) TYPE: NUCLEIC ACID
        ( C ) STRANDEDNESS: SINGLE
        ( D ) TOPOLOGY: UNKNOWN     ( i i ) MOLECULE TYPE:
        ( A ) DESCRIPTION: OLIGONUCLEOTIDE     ( i i i ) HYPOTHETICAL: NO     ( i v ) ANTI-SENSE: NO     ( v i ) ORIGINAL SOURCE:
        ( A ) ORGANISM: HUMAN
        ( C ) INDIVIDUAL ISOLATE: NK 3.3 CELL     ( i x ) FEATURE:
        ( A ) NAME/KEY:
        ( B ) LOCATION:
        ( C ) IDENTIFICATION METHOD:
        ( D ) OTHER INFORMATION: The N at nucleotides
            1 and 7 is inosine (I); the N at
            nucleotide 3 is G or T; and the N at
            nucleotides 4, 9, 10, 13, and 19 is A or
            G.

( x i ) SEQUENCE DESCRIPTION:SEQ ID NO:4:

NCN NCT NAN NTG NTA CAT NTC ATA                                        24

( 2 ) INFORMATION FOR SEQ ID NO:5:

( i ) SEQUENCE CHARACTERISTICS:
        ( A ) LENGTH: 24 BASE PAIRS
        ( B ) TYPE: NUCLEIC ACID
        ( C ) STRANDEDNESS: SINGLE
        ( D ) TOPOLOGY: UNKNOWN     ( i i ) MOLECULE TYPE:
        ( A ) DESCRIPTION: OLIGONUCLEOTIDE     ( i i i ) HYPOTHETICAL: NO     ( i v ) ANTI-SENSE: NO     ( v i ) ORIGINAL SOURCE:
        ( A ) ORGANISM: HUMAN
        ( C ) INDIVIDUAL ISOLATE: NK 3.3 CELL     ( i x ) FEATURE:
        ( A ) NAME/KEY:
        ( B ) LOCATION:
        ( C ) IDENTIFICATION METHOD:
        ( D ) OTHER INFORMATION: The N at nucleotides
            1 and 7 is C, T, A, or G; the N at
            nucleotide 3 is G or T; and the N at
            nucleotides 4, 9, 10, 13, and 19 is A or
            G.

( x i ) SEQUENCE DESCRIPTION:SEQ ID NO:5:

NCN NCT NAN NTG NTA CAT NTC ATA                                        24

( 2 ) INFORMATION FOR SEQ ID NO:6:

( i ) SEQUENCE CHARACTERISTICS:
        ( A ) LENGTH: 26 BASE PAIRS
        ( B ) TYPE: NUCLEIC ACID
        ( C ) STRANDEDNESS: SINGLE
        ( D ) TOPOLOGY: UNKNOWN (i i) MOLECULE TYPE:
    (A) DESCRIPTION: OLIGONUCLEOTIDE (i i i) HYPOTHETICAL: NO (i v) ANTI-SENSE: NO (v i) ORIGINAL SOURCE:
    (A) ORGANISM: HUMAN
    (C) INDIVIDUAL ISOLATE: NK 3.3 CELL (i x) FEATURE:
    (A) NAME/KEY:
    (B) LOCATION:
    (C) IDENTIFICATION METHOD:
    (D) OTHER INFORMATION: The N at nucleotides
        3, 6, 9, 11, and 18 is C, T, A, or G;
        the N at nucleotide 7 is C or T; and the
        N at nucleotide 15 is A or G.

(x i) SEQUENCE DESCRIPTION:SEQ ID NO:6:

GGN CCN NTN GTN AAN TCN GAA GAG AC   26